(12) United States Patent
English

(10) Patent No.: US 6,352,667 B1
(45) Date of Patent: Mar. 5, 2002

(54) METHOD OF MAKING BIODEGRADABLE POLYMERIC IMPLANTS

(75) Inventor: James P. English, Chelsea, AL (US)

(73) Assignee: Absorbable Polymer Technologies, Inc., Pelham, AL (US)

( * ) Notice: Subject to any disclaimer, the term of this patent is extended or adjusted under 35 U.S.C. 154(b) by 0 days.

(21) Appl. No.: 09/379,618

(22) Filed: Aug. 24, 1999

(51) Int. Cl.[7] .................................................. B29C 45/00
(52) U.S. Cl. .................................. 264/328.17; 623/901
(58) Field of Search ........................ 264/328.6, 328.17; 623/11, 901

(56) References Cited

U.S. PATENT DOCUMENTS

| | | |
|---|---|---|
| 4,190,711 A | 2/1980 | Zdrahala |
| 4,190,720 A | 2/1980 | Shalaby |
| 4,810,775 A | 3/1989 | Bendix et al. |
| 4,838,267 A | 6/1989 | Jamiolkowski et al. |
| 4,889,119 A | 12/1989 | Jamiolkowski et al. |
| 5,037,597 A * | 8/1991 | McGinley |
| 5,037,950 A | 8/1991 | Bezwada et al. |
| 5,225,129 A | 7/1993 | van den Berg |
| 5,275,601 A | 1/1994 | Gogolewski et al. |
| 5,349,046 A | 9/1994 | Beshouri et al. |
| 5,397,572 A | 3/1995 | Coombes et al. |
| 5,470,340 A | 11/1995 | Bezwada et al. |
| 5,492,697 A | 2/1996 | Boyan et al. |
| 5,492,997 A | 2/1996 | Grijpma et al. |
| 5,514,322 A | 5/1996 | Noritake |
| 5,668,234 A | 9/1997 | Rhodes et al. |
| 5,723,085 A * | 3/1998 | Abrams et al. |
| 5,741,331 A * | 4/1998 | Pinchuk |
| 5,981,619 A * | 11/1999 | Shikinami et al. |
| 6,028,164 A * | 2/2000 | Loomis |

* cited by examiner

Primary Examiner—Jill L. Heitbrink
(74) Attorney, Agent, or Firm—Nath & Associates PLLC; Gary M. Nath; Jerald L. Meyer

(57) ABSTRACT

A method of making a biodegradable polymeric implant comprising the steps of aseptically mixing at least one monomer with at least one catalyst to form a polymerization mixture, injecting the polymerization mixture into a sterile mold, and polymerizing and/or cross-linking the polymerization mixture in the sterile mold to form a sterilized biodegradable polymeric implant. Additives may be included in the polymerization mixture as needed.

67 Claims, 2 Drawing Sheets

METHOD OF MAKING BIODEGRADABLE POLYMERIC IMPLANTS

BACKGROUND OF THE INVENTION

1. Field of the Invention

This invention relates to a method of making a sterile biodegradable polymeric implant in which polymerization takes place in a mold, and to the implants produced therefrom.

2. Description of the Prior Art

In 1998, a National Health Interview Survey estimated that 32 million musculoskeletal injuries are reported in the United States each year. Surgical operations are required for more than 3 million cases with almost 40% involving fracture fixation or arthroplasties. Of those patients with an implanted fixation device, there are a great number of reported problems.

There are a large number of synthetic materials that are classified as bone repair devices used to initiate bone regeneration. Currently, the preferred materials used to initiate bone regeneration are metals, including stainless steel and titanium alloys. The strength, durability, shortened healing time, and exact repositioning of the fractured bone associated with these devices are among the greatest advantages. In the initial stages of healing, the high stiffness of the metals is preferred for the rigid fixation of the fracture. Unfortuantely, the continued stiffness throughout healing may impede bone remodelling. Additionally, other undesirable factors, including "stress-shielding," sensitization, corrosion and implant removal, related to the use of metallic materials have led to continued research for more suitable materials.

Biodegradable polymers have been considered in a variety of medical applications. Biodegradable polymers have proved successful as fracture fixation devices (implants), as well as suture materials, cardiovascular devices and drug delivery systems.

Traditional methods of preparing polymers, whether or not used as implantation devices, include bulk or melt polymerization, and solution polymerization. A polymer made by these processes must then be formed into the final usable product by a conventional molding technique, such as injection molding, compression molding or extrusion followed by sterilization. There are a number of problems associated with conventional manufacturing and sterilization processes of biodegradable polymers. These generally center around decreases in molecular weight of the polymer (which equates to a decrease in the mechanical strength) and the introduction of toxic substances (such as processing solvents and sterilization reagents) into a mammalian body.

One method of producing biodegradable implants is melt processing. For example, Bezwada et al., U.S. Pat. No. 5,470,340, discloses surgical devices made from copolymers of p-dioxanone and a prepolymer of p-dioxanone and a lactide or glycolide. The surgical devices are formed by conventional melt processing techniques. Additionally, Bezwada et al., U.S. Pat. No. 5,037,950 discloses bioabsorbable sutures and coatings for sutures made from copolymers of polyalkylene carbonate and ρ-dioxanone.

Melt processing involves extrusion or injection molding at high temperatures, introducing the possibility of thermal degradation and a subsequent reduction in the molecular weight of the polymer. Also, the crystallinity of the polymer, which directly impacts the mechanical properties of the device, is lost during melt processing and must be reformed to the desired degree by post injection processes that can be very difficult to control. Additionally, the melt viscosity of the polymer is proportional to the molecular weight of the polymer, making it very difficult to manufacture high molecular weight parts with detailed or complex geometry by melt processing.

Most biodegradable polymers can also be processed by solution processing. The low temperatures associated with this method eliminates the threat of thermal degradation. However, residual solvent could be toxic and elicit unfavorable tissue responses. Also, only fibers and films can normally be made by this technique. Bendix et al., U.S. Pat. No. 4,810,775, discloses a method of purifying resorbable polymers by solution processing. The purified polymers are used for medicinal purposes and are formed into their objects of use by compression molding.

Gel casting processes were developed to produce biological polymeric implants based on the principles used in solution processing. The polymer is dissolved in a solvent and cast into a mold allowing gel formation. The polymer is then removed from the mold and dried to obtain the solid implant. However, complete extraction of the solvent must be attained to ensure no toxins are introduced into the mammalian body in which the implant is implanted. Gogolewski et al., U.S. Pat. No. 5,275,601, discloses resorbable polymer bone screws and bone plates made from polyhydroxyacids, including polylactides. The implant devices are made by injection molding, compression molding, extrusion and/or gel processing the polymer. Similarly, Coombes et al., U.S. Pat. No. 5,397,572, discloses biodegradable implantation devices made from gelling a solution of a single polylactide enantiomer. The devices are made by dissolving the polymer in a solvent, casting the dissolved polymer in a mold, forming a gel in situ, removing the gel from the mold, and drying to obtain the solid implantation device. Boyan et al., U.S. Pat. No. 5,492,697, discloses the same process for making biodegradable implants of polylactic acid-polyglycolic acid copolymers.

A further technique developed for preparing polymers is reaction injection molding. Reaction injection molding has been used to form a number of different objects from a number of different polymers. For example, Beshouri et al., U.S. Pat. No. 5,349,046, discloses using reaction injection molding techniques to form β-lactone polymers useful as automotive parts, housewares, appliances, electrical components and sporting goods. About 60–85% of the polymerization takes place in the mold.

Similarly, Rhodes et al., U.S. Pat. No. 5,668,234, discloses using reaction injection molding techniques to form polymers of methyl methacrylates, lactams, lactones or acrylamides, useful for sanitary or bathroom items, such as sinks, bathtubs, shower stalls, tabletops and the like. About 90–95% of the polymerization takes place in the mold.

Further, Zdrahala et al., U.S. Pat. No. 4,190,711, discloses using reaction injection molding techniques to form thermoplastic polyether polyurethane elastomers useful in the production of automotive body panels, gears, seals and the like. Noritake et al., U. S. Pat. No. 5,514,322, discloses using reaction injection molding techniques for forming thermoplastic resins of lactams, lactones and carbonates.

Grigpma et al., U.S. Pat. No. 5,492,997, discloses the possibility of using reaction injection molding techniques to form biological medical implants consisting of copolymers of lactone and cyclic carbonate.

Conventional methods of sterilizing a biodegradable implant include treating with ethylene oxide or exposing to ionizing radiation. Such methods are used prior to the implant being implanted into a mammalian body. Sterilization processes can affect the performance of a biodegradable implant. Changes in both molecular weight and mechanical properties are observed with current sterilization techniques.

Most biodegradable implants are sterilized by an ethylene oxide treatment. Jamiolkowski et al., U.S. Pat. No. 4,838,267, discloses melt extrusion of block copolymers of glycolide and p-dioxanone to form surgical filaments. The filaments are then treated with ethylene oxide in order to sterilize them. Also, Jamiolkowski et al., U.S. Pat. No. 4,889,119, discloses injection molding a polymer with high lactide content and a polymer with a high glycolide content to form a surgical fastener. The fastener is then packaged and sterilized by conventional means. The low temperature and low humidity conditions of ethylene oxide treatment do not appear to present problems to the mechanical properties. However, toxic residues and possible byproducts must be removed before implantation, otherwise an inflamatory response may occur.

Electron beam or gamma radiation is effective in sterilizing bulk materials at low temperatures without chemical residues. However, chain scission of the biodegradable polymers by the high-energy radiation causes pre-degradation and a subsequent reduction in mechanical strength of the resultant implant. Shalaby et al., U.S. Pat. No. 4,190,720, discloses a polymeric material that is biodegradable and sterilizable with radiation. The polymeric material, though, is sterilized in a separate step following the formation of the implant.

Van den Berg, U.S. Pat. No. 5,225,129, discloses reaction injection molding cyclic monomers and catalysts to form a biodegradable polymeric material. Van den Berg further discloses the possibility of lining the mold with a flexible bag into which the mixture is injected and which, if sealed prior to polymerization, may form a sterile implant. However, the bag is needed in order to prepare a sterile implant.

Therefore, there remains a need for a method for making biodegradable polymeric implants that do not require post-formation sterilization of the implant, as well as a method in which a lining is not needed in the mold in order to form the sterile biodegradable implant. In addition, there is a need for a method in which sterile biodegradable polymeric implants can be manufactured in a one-step polymerization process from inexpensive raw materials. There is a further need for a method of producing high molecular weight implants with great detail and in which the crystallinity of the polymer is easily controlled.

There is also a need for a method in which sterile biodegradable implants made from block copolymers and sterile biodegradable implants made from cross-linked polymers can be manufactured in an inexpensive one-step manufacturing process.

SUMMARY OF THE INVENTION

Applicant has unexpectedly discovered a novel method of making a biodegradable polymeric implant comprising the steps of:
a) mixing at least one monomer and at least one telechelic polymer with at least one catalyst to form a polymerization mixture;
b) injecting said polymerization mixture into a mold in the shape of the desired implant; and
c) polymerizing said polymerization mixture in said mold to form a biodegradable polymeric implant.

Another embodiment of the inventive subject matter is a method of making a biodegradable polymeric implant comprising the steps of:
a) mixing at least one crosslinking agent and at least one telechelic polymer with at least one catalyst to form a crosslinkable polymerization mixture;
b) injecting said crosslinkable polymerization mixture into a mold in the shape of the desired implant; and
c) crosslinking said polymerization mixture in said mold to form a crosslinked biodegradable polymeric implant.

A further embodiment of the inventive subject matter is a method of making a biodegradable polymeric implant comprising the steps of:
a) aseptically mixing at least one monomer and at least one telechelic polymer with at least one catalyst to form a polymerization mixture;
b) aseptically injecting said polymerization mixture into an unlined sterile mold in the shape of the desired implant; and
c) polymerizing said polymerization mixture in said unlined sterile mold to form a sterile biodegradable polymeric implant.

In a still further embodiment of the present inventive process, the method is carried out aseptically and the biodegradable implant formed is sterile.

The present inventive subject matter is also drawn to the polymeric implants produced by the method. The polymeric implants may exhibit high tensile strengths and high inherent viscosities.

In addition to the implants exhibiting high tensile strengths and inherent viscosities, an advantage of the present inventive method is that biodegradable polymeric implants can be manufactured in a one-step polymerization process from inexpensive raw materials without the use of a liner in the mold. Another advantage of the present inventive method is that high molecular weight parts can be made with greater detail than with conventional injection molding because the polymerization mixture has a low viscosity when it enters the mold. A further advantage of the present inventive subject matter is that the crystallinity, biodegradation, chemical, physical and mechanical properties can be more easily controlled by the use of the telechelic polymers and/or cross-linking agents.

DETAILED DESCRIPTION OF THE INVENTION

As used herein, the expression "mammal" includes without limitation any mammalian subject, such as mice, rats, guinea pigs, cats, dogs, human beings, cows, horses, sheep or other livestock.

"Reaction injection molding" is a process used for some polymerization reactions in which the polymer is formed directly in a mold. Because polymerization occurs directly in the mold, low filling pressures and mold temperatures are involved which allows for molds to be made of less durable, less expensive materials such as aluminum and castable metals. Reaction injection molding also obviates the need for conventional molding techniques to form the final implant since polymerization takes place in the mold.

"Polymerization mixture" is a mixture that contains at least one telechelic polymer and at least one catalyst. In addition to the telechelic polymer and catalyst, a polymerization mixture may also include, without limitation, one or more monomers, initiators, cross-linking agents, and/or one or more other additives as described hereinbelow.

"Aseptically" means free from pathogenic microorganisms or blood-poisoning conditions. Pathogenic microorganisms include but are not limited to bacteria, mycoplasmas, viruses, molds, yeasts and protozoans. Blood-poisoning conditions include but are not limited to mycotoxins; dinoflagellate toxins; algal toxins; endotoxins; molecular components of bacteria, mold and yeast; biological excretions and secretions; hair; skin; dander; dust; and trace metals.

As used herein, "sterile" also means free from pathogenic microorganisms. Aseptic mixing and sterility are important in order to keep the mammalian body in which the biodegradable implant is inserted from becoming infectious or reacting negatively to the implant.

"Telechelic polymer" means a low-molecular weight polymer having at least one reactive end group.

The present inventive subject matter is drawn to a method of making a biodegradable polymeric implant. "Biodegradable" means capable of being biologically decomposed. A biodegradable polymer differs from a non-biodegradable polymer in that a biodegradable polymer can be biologically decomposed into units which may be either removed from the biological system and/or chemically incorporated into the biological system. Generally, the units of decomposition are the polymer's monomeric units. It is important that the biodegradable polymer decompose into non-toxic units.

Figure 1:
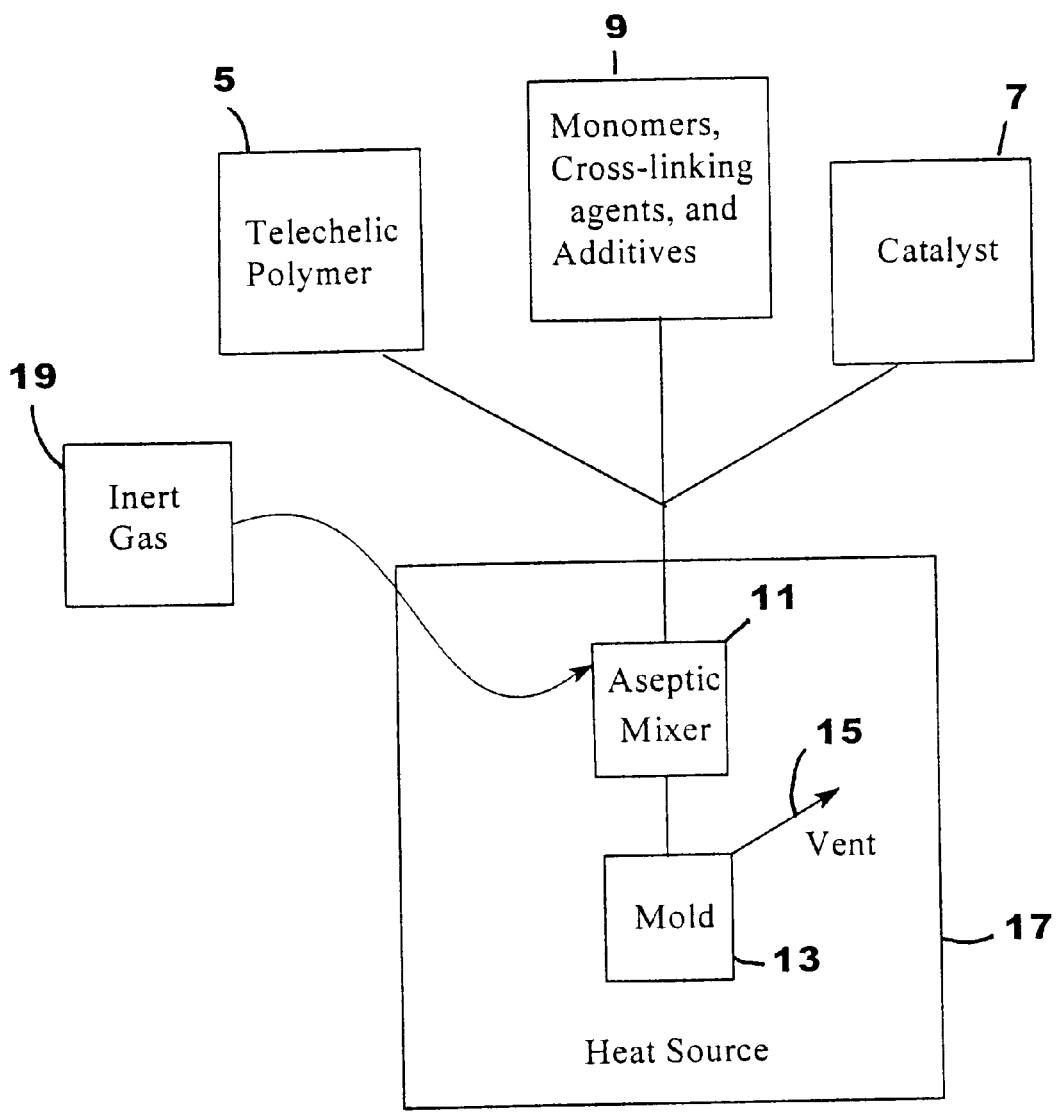
FIG. 1 is a flow diagram of the method of the present inventive subject matter.

The method of the present inventive subject matter overcomes the conventional problems associated with manufacturing and sterilizing biodegradable implants. FIG. 1 is a flow diagram of the method of the present inventive subject matter. As depicted, the present inventive subject matter is drawn to a method of making a biodegradable polymeric implant comprising the steps of mixing 11 at least one telechelic polymer 5 with at least one monomer 9 and a catalyst 7, or at least one cross-linking agent 9 and catalyst 7, to form a polymerization mixture, injecting the polymerization mixture into a mold 13, and polymerizing and/or cross-linking the polymerization mixture in the mold 13 to form a biodegradable polymeric implant. The mold 13 and mixing vessel 11 are in the presence of a heat source 17. The mold has a vent 15. A vacuum may be pulled on the mold using the vent, thus injecting the polymerization mixture into the mold from the mixing vessel. In the alternative, an inert gas 19 may be used to inject the polymerization mixture into the mold from the mixer. Alternatively, a sterile pump may be placed between the mixer and the mold to pump the polymerization mixture into the mold.

In a preferred embodiment of the present inventive subject matter, the telechelic polymers are mixed with the catalysts, monomers and/or cross-linking agents aseptically to form the polymerization mixture. The polymerization mixture is then injected into a sterile, unlined mold in the shape of the final implant. Polymerization and/or cross-linking takes place in the sterile, unlined mold, forming a sterile biodegradable polymeric implant. The method of the present inventive subject matter may be used to produce sterile biodegradable polymeric implants with high molecular weight and high tensile strength.

The method of the present inventive subject matter may be used to form a biodegradable implant made from any biodegradable polymer. Preferably, however, the monomers used in the present inventive process are selected from the group consisting of L-lactide; D-lactide; DL-lactide; glycolide; a lactone; epsilon caprolactone; dioxanone; a cyclic carbonate; trimethylene carbonate; a cyclic ether; a lactam; an acrylate ester; and a methacrylate ester. More preferably, the monomers used in the method of the present inventive subject matter are lactide and/or glycolide. The inventive subject matter also contemplates using mixtures of the above-listed monomers in the process.

Likewise, the telechelic polymers used in the present inventive process may be prepared from monomers selected from the group consisting of L-lactide; D-lactide; DL-lactide; glycolide; a lactone; epsilon-caprolactone; dioxanone; trimethylene carbonate; a cyclic carbonate; a cyclic ether; a lactam and mixtures thereof.

The telechelic polymers used in the present inventive process have at least one reactive end group. Preferably, the reactive end group are primary or secondary hydroxyl, primary or secondary amine, carboxylic, vinylic, acrylic or methacrylic. In addition, the telechelic polymer may be a polyether or a polyethylene glycol.

In addition, the telechelic polymers may be linear or branched homopolymers. In the alternative, the telechelic polymers may be linear or branched copolymers, with the copolymers being either random or block copolymers. The telechelic polymers may also contain reactive functional groups pendant to the polymeric chain. The telechelics generally have a weight average molecular weight in the range of 500 to 100,000 Daltons. Preferable, the telechelics have a weight average molecular weight in the range of 500 to 50,000 Daltons. More preferably, the telechelics have a weight average molecular weight in the range of 500 to 10,000 Daltons.

The telechelic polymers used in the present inventive process may be biocompatible, bioabsorbable, and/or biodegradable. Preferably, the telechelic polymer is selected from the group consisting of a biodegradable polyester, a biodegradable polycarbonatea biodegradable polyesteramide, a biodegradable polyesterether, and a biodegradable polyanhydride, and copolymers or mixtures thereof.

Biodegradable polymers used as medical implants have quite different physical, chemical, and mechanical properties depending on their intended application. For example, a polymeric implant intended for repair of osseous tissue, such as a bone screw, will need to be stronger, more rigid, and slower degrading than an implant intended for repair of soft tissue, such as a staple. Therefore, it is desirable to be able to prepare medical implant devices over a wide range of chemical, physical, and mechanical properties.

One method of achieving a wide range of properties which is particularly suited to the process of the present invention is through the use of block copolymers. To those skilled in the art, a convenient way of preparing block copolymers according to the present invention is to first prepare a telechelic polymer (a low-molecular weight polymer containing one or more reactive end groups) either outside of or within the aseptic mixer, adding additional monomers to the telechelic polymer within the aseptic mixer, and further reacting the telechelic polymer with the additional monomers to form a block copolymer. One non-limiting example of this method is to prepare a telechelic -OH terminated polymer by reaction of DL-lactide with a diol initiator such as ethylene glycol to yield an -OH terminated telechelic DL-lactide polymer. The -OH terminated telechelic DL-lactide polymer is amorphous. The telechelic DL-lactide polymer can then be further reacted with another monomer, for example, L-lactide to form a final ABA block copolymer with both crystalline zones from the A (L-lactide) blocks and amorphous zones from the B (original DL-lactide) block. This ABA block copolymer will have significantly different chemical, physical, and mechanical properties from the separate homopolymers or random copolymers of these two monomers.

If the telechelic polymer has only one reactive end group, an AB block copolymer is obtained having even different chemical, physical and mechanical properties from the ABA block copolymer. An example of an AB block copolymer is obtained by using an -OH terminated polyethylene glycol (PEG-OH) as the telechelic polymer and further reacting the PEG-OH with a monomer such as L-lactide to yield a final lactide/PEG block copolymer. The PEG segment significantly increases the hydrophilicity of the final block copolymer, thus modifying the chemical, physical and mechanical properties of the final polymer and particularly enhancing its biodegradability.

Yet another method of conveniently modifying the properties of the polymeric implant that is particularly suited to the process of the present invention is through the use of cross-linked polymers. The telechelic polymer can also be reacted with various cross-linking agents to form a final cross-linked polymer which adds rigidity to the polymer chains thus increasing the elastic modulus. For example, the DL-lactide telechelic diol in the example above can be reacted with additional monomers as in the example given while simultaneously reacting with a prescribed quantity of bislactone or bislactide (the quantity of which governs the degree of crosslinking) thus yielding a crosslinked structure. Such reactions can easily be carried out in the process of the present invention.

The cross-linking agent used in the present inventive process may be unsaturated or polyunsaturated. Preferably, the cross-linking agent contains acrylic unsaturation, methacrylic unsaturation or vinylic unsaturation. The cross-linking agent may also be selected from the group consisting of a bislactone, a spirolactone, and a bislactide. In addition, the cross-linking polymerization mixture may contain a polyhydroxy compound selected from the group consisting of sugars, trimethylol propane and pentaerythritol to further increase crosslink density.

An attractive characteristic of these block copolymers and cross-linked polymers is that the products of degradation are non-toxic products that are readily eliminated by the body.

Polymerization of the telechelic polymers and monomers may occur in many ways, such as by free radical polymerization, anionic polymerization or cationic polymerization. Polymerization may also take place in the solid state. During solid state polymerization, crystallization of the polymer is achieved by maintaining a temperature greater than the melting point of the monomer and the glass transition temperature of the polymer, but lower than the polymer's melting point. Polymerization factors that affect the final molecular weight and mechanical properties include type and percentage of catalyst, type and percentage of initiator, and time and temperature of reaction. Due to the thermodynamic instability of biodegradable polyesters, melt processing and sterilization techniques typically cause some degradation of the polymer, with a subsequent decrease in the ultimate mechanical strength of the device. Due to the lower temperatures in the single step process of the invention, and the lack of further melt and sterilization processing, degradation is greatly reduced.

In a preferred feature of the process of the invention, one or more additives are included in the mixing step of the process. Additives which may be introduced in the mixing step include conventional and well-known initiators, cross-linkers, fillers, reinforcing fibers, microparticles, microspheres, microfibers, plasticizers, crystal-nucleating agents and biologically active substances. The present inventive process also contemplates mixtures of any number of the above additives.

An initiator introduced in the mixing step may be monofuntional or polyfunctional, depending on the desired characteristics of the resultant polymer. In addition, the initiator may be polymeric.

A reinforcing fiber may be introduced into the monomeric mixture in order to supply additional strength to the implant. Many types of reinforcing fibers may be introduced into the monomeric mixture in the mixing step. The reinforcing fibers may be made of carbon or a biodegradable polymer. Also, the reinforcing fibers may be inorganic.

A plasticizer may also be introduced into the monomeric mixture in the mixing step of the present inventive process. Preferably, the plasticizer is a low-molecular-weight, biodegradable polymer such as a copolymer of lactide and caprolactone. However, any biocompatible plasticizer may be used.

Examples of crystal-nucleating agents which may be introduced into the monomeric mixture include calcium metaphosphate, micronized polylactide, polyglycolide, or any micronized biodegradable polymer. Other such crystal-nucleating agents are also within the scope of the present inventive subject matter. The present inventive process contemplates use of mixtures of any number of the above crystal-nucleating agents.

The biologically active substance which may be introduced in the mixing step can vary greatly with the purpose of the implant. The term "biologically active substance" includes, without limitation, medicaments; vitamins; mineral supplements; substances used for the treatment, prevention, diagnosis, cure or mitigation of disease or illness; substances which affect the structure or function of the body; or drugs. The biologically active substances are used in amounts that are therapeutically effective.

The biologically active substances may first be encapsulated into microcapsules, microspheres, microparticles, microfibers, reinforcing fibers and the like to facilitate mixing and achieving controlled, extended, delayed and/or sustained release. Encapsulating the biologically active substance may also protect against the degradation of the biologically active substance during formation of the polymer or prepolymer.

Additionally, the drugs may be pendantly attached to the resultant polymeric implant. The attachment may be facilitated through covalently linking the drug to the polymeric implant. In the alternative, the drugs may be attached to the polymeric implant through the use of hydrogen bonding.

Examples of drugs include, without limitation, analgesics; anti-infective agents; antineoplastic agents; cardiovascular agents; hematological agents; hormones and hormone modifiers; immunobiological agents; musculoskeletal agents; neurological agents; ophthalmic agents; steroids; respiratory agents; psychotropic agents; and toxicology agents.

In a preferred embodiment of the invention, the biologically active substance is controllably released into a mammal when the biodegradable polymeric implant produced by the inventive process is implanted in a mammal. Preferably, the biodegradable polymeric implant is used to close a discontinuity in the tissue in the mammalian body. The rate of release of the biologically active substance into the mammalian body is dependent on, among other things, the type and molecular weight of the polymer formed by the inventive process and the degradation rate of the polymer in the mammalian body. The degradation of the polymer, and therefore of the implant, enables proper healing of the tissue. In the case of osseous tissue, the degradation of the polymer, and therefore of the implant, enables proper healing of a fracture site by allowing gradual transfer of load to the bone. Thus, it is ideal to control the degradation rate to be equivalent to the healing rate of the tissue. If degradation occurs too quickly, the stability of the implant is jeopardized and loads may be transferred to the tissue before sufficient healing occurs. The rapid degradation may impede tissue regeneration.

The present inventive subject matter is also drawn to the biodegradable polymeric implant produced by the inventive methods. The biodegradable polymeric implant may be in the form of a plate, pin, rod, screw, anchor, tack, arrow, staple, button or other implantable shape.

The polymers formed by the method of the present inventive subject matter have shown surprising high mechanical strengths. The mechanical properties are highly influenced by the material properties such as polymer type, molecular weight, crystallinity and residual monomers. A highly crystalline material with a high molecular weight and free of monomeric impurities generally has high strength.

One measure of a material's mechanical strength is its tensile strength. Tensile strength is a measure of the rupture strength per unit area of a material subjected to a specified dynamic load. Generally, the higher the molecular weight of a polymer, the greater the tensile strength. The prior art polylactide polymers used in implants have shown tensile strengths approaching 70 MPa, while the polylactide polymers produced by the method of the present inventive subject matter have shown tensile strengths in excess of 76 Mpa and preferably from about 76 MPa to about 82 MPa, as is shown by the following examples.

The polylactide polymers formed by the method of the present inventive subject matter can also have high inherent viscosities and therefore high molecular weights. As the molecular weight of a polymer increases, there is a corollary increase in the inherent viscosity of the polymer. Higher molecular weight polymers are possible due to the fact that the polymerization takes place in the mold and the polymer chains are not broken by the conventional molding techniques. The high molecular weight polylactide polymers have a weight average molecular weight of about 1,000,000 by gel permeation chromatography and about 700,000 by laser light scattering. Normally, high melt viscosities of high molecular weight polymers restricts their melt flow, making it difficult to mold by injection molding. The viscosity of the polymerization or prepolymer mixture in the present inventive method is low at the time it enters the mold. This also allows the implants resulting from the present inventive method to have a greater degree of detail.

The following examples are illustrative of preferred embodiments of the invention and are not to be construed as limiting the invention thereto. All percentages are given in weight percent, unless otherwise noted and equal a total of 100%.

EXAMPLES

Example 1

Evaluation of Various Polymerization Conditions

A magnetic spin bar was placed in a clean dry 20 mL glass vial. A catalyst solution containing about 1.30 grams of stannous 2-ethyl hexanoate (stannous octoate) in 10 mL of dry toluene was prepared. A volume of the catalyst solution equivalent to 0.02%–0.085% of the L-lactide monomer to be used was injected at room temperature into the glass vial with a microliter syringe. An appropriate quantity of L-lactide monomer was added to the glass vial under a dry inert atmosphere. The vial was sealed and placed in an oil bath at a controlled temperature (110–125° C.). After the monomer had melted, the vial containing the monomer/catalyst mixture was magnetically stirred by the spin bar until viscous (1–4 hours). At these conditions, the polymer crystallized as the polymerization proceeded, indicating solid state polymerization. After the specified reaction time (48–96 hours), the vial was removed from the oil bath and allowed to cool to room temperature.

Specimens were removed from the samples and the inherent viscosity ($\eta$) was determined in chloroform based on a modified version of ASTM D-2857. Samples obtained from the test polymers were dissolved in chloroform obtained from Burdick and Jackson, making ~0.5% weight/volume polymer solutions. The samples were agitated overnight. Three trials of the relative viscosity ($\eta_{rel}$) of solution was measured using a Cannon Fenske viscometer at 30° C. The mean average of the relative viscosity was used in the following equation to calculate the inherent viscosity:

$$\eta = \ln(\eta_{rel})/\text{concentration}$$

The conditions and results of various trials are given in Table 1.

TABLE 1

REACTION CONDITIONS USED FOR POLY(L-LACTIDE) TRIALS

| Sample | Catalyst Amount, % Stannous Octoate | Reaction Time, hours | Reaction Temp., ° C. | Inherent Viscosity, dL/g |
|---|---|---|---|---|
| A108-73C | 0.0282 | 48 | 115 | 0.59 |
| A108-99A | 0.0282 | 72 | 115 | 3.48 |
| A108-99C | 0.0282 | 96 | 115 | 3.90 |
| A108-73A | 0.0563 | 48 | 115 | 1.19 |
| A108-65 | 0.0563 | 72 | 115 | 3.60 |
| A108-99B | 0.0563 | 96 | 115 | 3.90 |
| A108-73B | 0.0845 | 47 | 115 | 1.93 |
| A108-77B | 0.0845 | 72 | 115 | 2.22 |
| A108-77A | 0.0845 | 96 | 115 | 2.89 |

Example 2

Molding of Mechanical Test Specimens

A laboratory-scale, proof-of-principle molding process apparatus was constructed to include the steps of the present inventive subject matter. An aluminum mold was constructed for the process in the shape of a standard tensile test specimen. The mixing vessel and all connecting tubing and fittings were made of stainless steel. The mixing vessel and all apparatus were cleaned and dried at about 120° C. A dry magnetic spin bar was placed inside the mixing vessel. Next, an amount of catalyst solution equivalent to 0.0563 wt % based on the weight of the monomer was added to the mixing vessel. The mixing vessel was then charged with 20–25 grams of monomer under an inert atmosphere. The mixing vessel was closed and placed in an oil bath supported by a magnetic stirrer. The remaining parts of the process apparatus were preassembled inside a convection oven. The reactants were then melted and mixed.

After mixing, the mixing vessel was removed from the oil bath and connected to the remaining parts of the process apparatus inside the convection oven. The entire assembly was then allowed to equilibrate for several minutes. Pressure was then applied to the mixing vessel to force the reaction mixture into the mold. The reaction mixture was then allowed to polymerize inside the mold for the desired period of time. At the end of the polymerization cycle, the mold was allowed to cool and the finished parts were removed. Five trials of poly(L-lactide) are listed below in Table 2.

The tensile properties of the molded parts were determined on an MTS Mechanical Tester equipped with an extensometer following the guidelines of ASTM D-638. The tensile properties are listed in Table 3. The inherent viscosity of the molded parts was determined after mechanical testing was complete. Samples were obtained from the fracture site and dissolved in chloroform, making ~0.2% weight/volume diluted polymer solutions. Calculation of inherent viscosity was determined as in Example 1 above.

TABLE 2

MOLDING CONDITIONS USED FOR POLY(L-LACTIDE) TENSILE SPECIMENS

| Sample | Catalyst Amount, % Stannous Octoate | Molding Temp. °C. | Molding Time, Hours |
| --- | --- | --- | --- |
| A108-67 | 0.0563 | 115 | 72 |
| A108-87 | 0.0563 | 115 | 72 |
| A108-89 | 0.0563 | 115 | 72 |
| A113-03 | 0.0563 | 115 | 72 |
| A113-09 | 0.0563 | 115 | 72 |

TABLE 3

TENSILE PROPERTIES OF MOLDED SPECIMENS

| Sample | Inherent Viscosity, dL/g | Tensile Strength, psi (MPa) | Elastic Modulus, psi |
| --- | --- | --- | --- |
| A108-67 | 5.80 | 11,500 (79.3) | 8.43E + 05 |
| A108-87 | 5.15 | 11,100 (76.5) | 8.61E + 05 |
| A108-89 | 5.25 | 11,600 (80.0) | 9.76E + 05 |
| A113-03 | 5.31 | 11,800 (81.4) | 8.87E + 05 |
| A113-09 | 4.93 | 11,400 (78.6) | 8.60E + 05 |

Example 3

Figure 2:
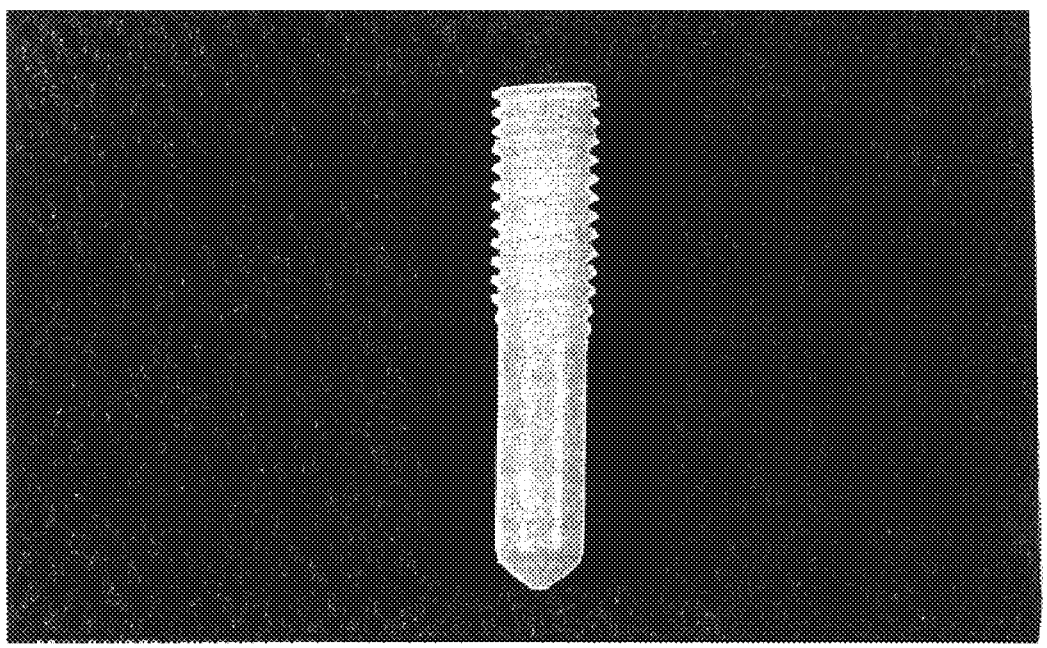
FIG. 2 is a photograph of a biodegradable implant produced by the method of the present inventive subject matter.

Molding of a Screw-Shaped Part A mold was prepared in the shape of a threaded rod 5/16 inches by 18 threads per inch. A finished part was molded in the shape of the screw using the same conditions as used in Example 2. The molded part showed detailed reproduction of the treaded mold. FIG. 2 shows the resultant molded part.

Example 4

Preparation of an ABA Block Copolymer of L-lactide ("A" Blocks) and Epsilon-Caprolactone ("B" Blocks) Using a Method Suited to the Reaction Injection Molding Process An ABA block copolymer of L-lactide and epsilon-caprolactone having a theoretical molar composition of 85% epsilon-caprolactone and 15% L-lactide was prepared by first combining 122.67 grams of epsilon-caprolactone with 0.0591 grams of 1,6 hexane diol in a stirred reaction vessel heated in an oil bath at 145° C. The reaction vessel was evacuated and backfilled with dry argon 5 times. A bubbler was attached to the reaction vessel to maintain a slight positive argon pressure through the entire polymerization reaction. After 10 minutes of stirring, 0.075 grams of stannous 2-ethyl hexanoate dissolved in toluene (1.3159 g SnOct/10 ml toluene) was added. The mixture was allowed to react with continued stirring under the dry argon atmosphere for 2.75 hours at 145° C. to form a telechelic -OH terminated polycaprolactone as the "B" block for the final ABA block copolymer. After 2.75 hours, the reaction mixture had visibly increased significantly in viscosity, indicating that polymerization of the epsilon-caprolactone had taken place and the telechelic polycaprolactone had formed. At this time 27.34 grams of molten L-lactide monomer was added to the reaction vessel under a dry argon atmosphere to react with the telechelic polycaprolactone and form the "A" blocks of the desired ABA block copolymer.

The telechelic polycaprolactone dissolved into the molten L-lactide monomer as evidenced by the formation of a clear lower viscosity polymerization mixture. Stirring of the polymerization mixture continued for an additional 1.25 hours at 145° C. The polymerization mixture had then visibly increased in viscosity, but still remained fluid enough to be injectable in the reaction injection molding process. Stirring was discontinued and the polymerization mixture was continually heated, without further stirring, inside the reaction vessel for a total heating time of 20 hours. The reaction vessel was then removed from the oil bath and allowed to cool to room temperature. The polymer was in the shape of the reaction vessel.

The final composition of the polymer was determined by $^1$H-NMR to be 85% caprolactone and 15% L-lactide in excellent agreement with the theoretical. The inherent viscosity was determined to be 1.68 dL/g in chloroform at 30° C.

Example 5

Preparation of an ABA Block Copolymer of L-lactide and Epsilon Caprolactone Where the "B" Block is a Random Copolymer of L-lactide and Epsilon-Caprolactone and the "A" Blocks are L-lactide, Using a Method Suited to the Reaction Injection Molding Process An ABA block copolymer of L-lactide and epsilon-caprolactone having a final theoretical molar composition of 40% epsilon-caprolactone and 60% L-lactide was prepared by first combining 51.79 grams of epsilon-caprolactone and 21.80 grams of L-lactide with 0.0591 grams of 1,6 hexane diol in a stirred reaction vessel heated in an oil bath at 145° C. The reaction vessel was evacuated and backfilled with dry argon 3 times. A bubbler was attached to the reaction vessel to maintain a slight positive argon pressure through the entire polymerization reaction. After 13 minutes of stirring, 0.075 grams of stannous 2-ethyl hexanoate dissolved in toluene (1.3202 g SnOct/10 ml toluene) was added. The mixture was allowed to react with continued stirring under the dry argon atmosphere for 2.66 hours at 145° C. to form a random telechelic -OH terminated 75/25 poly (caprolactone-co-L-lactide) as the "B" block for the final ABA block copolymer. After the 2.66 hours the reaction mixture had visibly increased significantly in viscosity indicating that polymerization of the epsilon-caprolactone and L-lactide had taken place and the random telechelic poly (caprolactone-co-L-lactide) had formed.

At this time 76.29 grams of molten L-lactide monomer was added to the reaction vessel under a dry argon atmosphere to react with the telechelic poly(caprolactone-co-L- lactide) to form the "A" blocks of the desired ABA block copolymer. The telechelic poly(caprolactone-co-L-lactide) dissolved into the molten L-lactide monomer as evidenced by the formation of a clear lower viscosity polymerization mixture. Stirring of the polymerization mixture was continued for an additional 1.3 hours at 145° C. The polymerization mixture had then visibly increased in viscosity, but still remained fluid enough to be injectable in the reaction injection molding process. Stirring was discontinued and the polymerization mixture was continually heated, without further stirring, inside the reaction vessel for a total heating time of 18 hours. The reaction vessel was then removed from the oil bath and allowed to cool to room temperature. The polymer was in the shape of the reaction vessel.

The final molar composition was determined by $^1$H-NMR to be 28% caprolactone and 72% L-lactide. The inherent viscosity was determined to be 1.52 dL/g in chloroform at 30° C.

The inventive subject matter being thus described, it will be obvious that the same may be varied in many ways. Such variations are not to be regarded as a departure from the spirit and scope of the inventive subject matter, and all such modifications are intended to be included within the scope of the following claims.

I claim:

1. A method of making a biodegradable polymeric implant comprising the steps of:
   a) mixing at least one monomer and at least one telechelic polymer with at least one catalyst to form a polymerization mixture;
   b) injecting said polymerization mixture into a mold in the shape of the desired implant; and
   c) polymerizing said polymerization mixture in said mold to form a biodegradable polymeric implant.

2. A method according to claim 1 wherein said method is carried out aseptically and said biodegradable polymeric implant formed is sterile.

3. A method according to claim 1 wherein the monomer is selected from the group consisting of L-lactide, D-lactide, DL-lactide, glycolide, a lactone, epsilon caprolactone, dioxanone, a cyclic carbonate, trimethylene carbonate, a cyclic ether, a lactam, an acrylate ester, a methacrylate ester and mixtures thereof.

4. A method according to claim 1 wherein the telechelic polymer is prepared from monomers selected from the group consisting of L-lactide, D-lactide, DL-lactide, glycolide, a lactone, epsilon caprolactone, dioxanone, a cyclic carbonate, trimethylene carbonate, a cyclic ether, a lactam, and mixtures thereof.

5. A method according to claim 1 wherein the telechelic polymer has at least one reactive end group.

6. A method according to claim 5 wherein the reactive end group is selected from the group consisting of a primary hydroxyl, a secondary hydroxyl, a primary amine, a secondary amine, a carboxyl, a vinylic, an acrylic and a methacrylic.

7. A method according to claim 1 wherein the telechelic polymer is a linear or branched homopolymer.

8. A method according to claim 1 wherein the telechelic polymer is a linear or branched copolymer.

9. A method according to claim 1 wherein the telechelic polymer is a random or block copolymer.

10. A method according to claim 1 wherein the telechelic polymer has a molecular weight in the range of 500 to 100,000 Daltons.

11. A method according to claim 1 wherein the telechelic polymer has a molecular weight in the range of 500 to 50,000 Daltons.

12. A method according to claim 1 wherein the telechelic polymer has a molecular weight in the range of 500 to 10,000 Daltons.

13. A method according to claim 1 wherein the telechelic polymer is biocompatible, bioabsorbable and/or biodegradable.

14. A method according to claim 1 wherein the telechelic polymer is selected from the group consisting of a biodegradable polyester, a biodegradable polycarbonate, a biodegradable polyesteramide, a biodegradable polyesterether, and a biodegradable polyanhydride.

15. A method according to claim 1 wherein the telechelic polymer is a polyether or a polyethylene glycol.

16. A method according to claim 1 wherein at least one additive is included in mixing step a), said additive being selected from the group consisting of initiators, crosslinkers, fillers, reinforcing fibers, microparticles, microspheres, microfibers, plasticizers, crystal-nucleating agents and mixtures thereof.

17. A method according to claim 16 wherein the crystal-nucleating agent is selected from the group consisting of calcium metaphosphate, a micronized biodegradable polymer such as polylactide or polyglycolide, and mixtures thereof.

18. A method according to claim 16 wherein said initiator is monofunctional.

19. A method according to claim 16 wherein said initiator is polyfunctional.

20. A method according to claim 16 wherein said plasticizer is a low-molecular-weight, biodegradable polymer.

21. A method according to claim 16 wherein said reinforcing fiber is made of carbon.

22. A method according to claim 16 wherein said reinforcing fiber is made of a biodegradable polymer.

23. A method according to claim 16 wherein said reinforcing fiber is inorganic.

24. A method according to claim 1 wherein at least one biologically active substance is included in mixing step a).

25. A method according to claim 24 wherein the biologically active substance is a drug.

26. A method according to claim 24 wherein said drug is selected from the group consisting of analgesics, anti-infective agents, antineoplastic agents, cardiovascular agents, hematological agents, hormones and hormone modifiers, immunobiological agents, musculoskeletal agents, neurological agents, ophthalmic agents, steroids, respiratory agents, psychotropic agents, and toxicology agents.

27. A method according to claim 24 wherein said biologically active substance is incorporated into a microparticle, microsphere, microfiber, or fiber prior to being mixed into the polymerization mixture.

28. A method according to claim 24 wherein said biologically active substance is attached to the polymeric implant formed.

29. A method according to claim 24 wherein the biologically active substance is controllably released into a mammal when said biodegradable polymeric implant is implanted in said mammal.

30. A method according to claim 1 wherein the biodegradable polymeric implant closes a discontinuity in tissues when implanted into a mammal.

31. A method according to claim 1 wherein the biodegradable polymeric implant is shaped in a form of a plate, pin, rod, screw, anchor, tack, arrow, staple, button, or other implantable shape.

32. A method of making a biodegradable polymeric implant comprising the steps of:

a) mixing at least one crosslinking agent and at least one telechelic polymer with at least one catalyst to form a crosslinkable polymerization mixture;

b) injecting said crosslinkable polymerization mixture into a mold in the shape of the desired implant; and c) crosslinking said polymerization mixture in said mold to form a crosslinked biodegradable polymeric implant.

33. A method according to claim 32 wherein said method is carried out aseptically and said biodegradable polymeric implant formed is sterile.

34. A method according to claim 32 wherein the crosslinking agent is selected from the group consisting of a bislactone, a spirolactone, and a bislactide.

35. A method according to claim 32 wherein the crosslinking agent is unsaturated or polyunsaturated.

36. A method according to claim 35 wherein the crosslinking agent contains acrylic, methacrylic, or vinylic unsaturation.

37. A method according to claim 32 wherein the crosslinkable polymerization mixture contains a polyhydroxy compound selected from the group consisting of sugars, trimethylol propane and pentaerythritol.

38. A method according to claim 32 wherein the telechelic polymer is prepared from monomers selected from the group consisting of L-lactide, D-lactide, DL-lactide, glycolide, a lactone, epsilon caprolactone, dioxanone, a cyclic carbonate, trimethylene carbonate, a cyclic ether, a lactam, and mixtures thereof.

39. A method according to claim 32 wherein at least one monomer is included in mixing step a).

40. A method according to claim 39 wherein the monomer is selected from the group consisting of L-lactide, D-lactide, DL-lactide, glycolide, a lactone, epsilon caprolactone, dioxanone, a cyclic carbonate, trimethylene carbonate, a cyclic ether, a lactam, an acrylate ester, a methacrylate ester, and mixtures thereof.

41. A method according to claim 39 wherein the crosslinkable polymerization mixture contains a polyhydroxy compound selected from the group consisting of sugars, trimethylol propane and pentaerythritol.

42. A method according to claim 32 wherein the telechelic polymer has at least one reactive end group.

43. A method according to claim 42 wherein the reactive end group is selected from the group consisting of a primary hydroxyl, a secondary hydroxyl, a primary amine, a secondary amine, a carboxyl, a vinylic, an acrylic and a methacrylic.

44. A method according to claim 32 wherein the telechelic polymer is a linear or branched homopolymer.

45. A method according to claim 32 wherein the telechelic polymer is a linear or branched copolymer.

46. A method according to claim 32 wherein the telechelic polymer is a random or block copolymer.

47. A method according to claim 32 wherein the telechelic polymer has a molecular weight in the range of 500 to 100,000 Daltons.

48. A method according to claim 32 wherein the telechelic polymer is biocompatible, bioabsorbable and/or biodegradable.

49. A method according to claim 32 wherein the telechelic polymer is selected from the group consisting of a biodegradable polyester, a biodegradable polycarbonate, a biodegradable polyesteramide, a biodegradable polyesterether, and a biodegradable polyanhydride.

50. A method according to claim 32 wherein the telechelic polymer is a polyether or a polyethylene glycol.

51. A method according to claim 32 wherein at least one additive is included mixing step a), said additive being selected from the group consisting of initiators, crosslinkers, fillers, reinforcing fibers, microparticles, microspheres, microfibers, plasticizers, crystal-nucleating agents and mixtures thereof.

52. A method according to claim 51 wherein the crystal-nucleating agent is selected from the group consisting of calcium metaphosphate, a micronized biodegradable polymer such as polylactide or polyglycolide, and mixtures thereof.

53. A method according to claim 51 wherein said initiator is monofunctional.

54. A method according to claim 51 wherein said initiator is polyfunctional.

55. A method according to claim 51 wherein said plasticizer is a low-molecular-weight, biodegradable polymer.

56. A method according to claim 51 wherein said reinforcing fiber is made of carbon.

57. A method according to claim 51 wherein said reinforcing fiber is made of a biodegradable polymer.

58. A method according to claim 51 wherein said reinforcing fiber is inorganic.

59. A method according to claims 32 wherein at least one biologically active substance is included in mixing step a).

60. A method according to claim 59 wherein the biologically active substance is a drug.

61. A method according to claim 60 wherein said drug is selected from the group consisting of analgesics, anti-infective agents, antineoplastic agents, cardiovascular agents, hematological agents, hormones and hormone modifiers, immunobiological agents, musculoskeletal agents, neurological agents, ophthalmic agents, steroids, respiratory agents, pschotropic agents, and toxicology agents.

62. A method according to claim 59 wherein said biologically active substance is incorporated into a microparticle, microsphere, microfiber, or fiber prior to being mixed into the polymerization mixture.

63. A method according to claim 59 wherein said biologically active substance is attached to the polymeric implant formed.

64. A method according to claim 59 wherein the biologically active substance is controllably released into a mammal when said biodegradable polymeric implant is implanted in said mammal.

65. A method according to claim 32 wherein the biodegradable polymeric implant closes a discontinuity in tissues when implanted into a mammal.

66. A method according to claim 32 wherein the biodegradable polymeric implant is shaped in a form of a plate, pin, rod, screw, anchor, tack, arrow, staple, button, or other implantable shape.

67. A method of making a sterile biodegradable polymeric implant comprising the steps of:

a) aseptically mixing at least one monomer and at least one telechelic polymer with at least one catalyst to form a polymerization mixture;

b) aseptically injecting said polymerization mixture into an unlined sterile mold in the shape of the desired implant; and c) polymerizing said polymerization mixture in said unlined sterile mold to form a sterile biodegradable polymeric implant.

* * * * *